(12) United States Patent
Endo (10) Patent No.: US 7,341,740 B2
(45) Date of Patent: Mar. 11, 2008

(54) HUMAN MITOCHONDRIAL PROTEINS AND POLYNUCLEOTIDE ENCODING THE PROTEINS

(75) Inventor: Hitoshi Endo, Tochigi (JP)

(73) Assignee: Japan Science and Technology Corporation, Saitama (JP)

( * ) Notice: Subject to any disclaimer, the term of this patent is extended or adjusted under 35 U.S.C. 154(b) by 117 days.

(21) Appl. No.: 11/344,194

(22) Filed: Feb. 1, 2006

(65) Prior Publication Data

US 2006/0246125 A1    Nov. 2, 2006

Related U.S. Application Data

(62) Division of application No. 10/470,554, filed as application No. PCT/JP01/09783 on Nov. 8, 2001, now Pat. No. 7,026,452.

(30) Foreign Application Priority Data

Jan. 31, 2001 (JP) ............................. 2001-024525

(51) Int. Cl.
*A61K 9/127* (2006.01)
(52) U.S. Cl. ...................... 424/450; 530/350
(58) Field of Classification Search ...................... None
See application file for complete search history.

(56) References Cited

U.S. PATENT DOCUMENTS 6,127,159 A    10/2000    Fuller et al.

FOREIGN PATENT DOCUMENTS

WO    99/57132    11/1999
WO    01/25274    4/2001

OTHER PUBLICATIONS

Ansger Satel et al., "Control of Mitochondrial Morphology by a Human Mitofusin", Journal of Cell Science, vol. 114, No. 5, pp. 867-874, 2001.
Yingying Tang et al., "Maintenance of Human Rearranged Mitochondrial DNAs in Long-Term Cultured Transmitochondrial Cells Lines", Molecular Biology of the Cell, vol. 11, No. 7, pp. 2349-2358, Jul. 2000.
Bowie et al., *Science*, vol. 247, pp. 1306-1310, 1990.
Wells, *Biochemistry*, vol. 29, pp. 8509-8517, 1990.
Y. Inoki et al., "Proteoliposomes Colocalized with Endogenous Mitochondria in Mouse Fertilized Egg", Biochemical and Biophysical Research Communications, vol. 278, No. 1, pp. 183-191, 2000 with two abstracts from National Library of medicine and Ideal Library.

*Primary Examiner*—Robert Landsman
*Assistant Examiner*—Gyan Chandra
(74) *Attorney, Agent, or Firm*—Wenderoth, Lind & Ponack, L.L.P.

(57) ABSTRACT

The invention of the present application provides an isolated and purified human mitochondrial protein comprising the amino acid sequence of SEQ ID NO: 2 or SEQ ID NO: 4, which is a novel human protein promoting aggregation and fusion of mitochondria. The present invention also provides a polynucleotide encoding such a mitochondrial protein, antibody against such a mitochondrial protein, and a proteoliposome composed of such a mitochondrial protein and lipid. Mitochondrial proteins are useful for clarifying causes of mitochondrial diseases as well as for developing preventive and therapeutic methods thereof. Furthermore, antibodies and probes derived from genes encoding such proteins are potentially useful materials for diagnosis of condition of mitochondria in particular diseases. Furthermore, proteoliposomes provide measures for specific transfer of foreign genes or drugs targeted toward mitochondria.

1 Claim, 2 Drawing Sheets

SEQUENCE LISTING

<160> NUMBER OF SEQ ID NOS: 4

<210> SEQ ID NO 1
<211> LENGTH: 2754
<212> TYPE: DNA
<213> ORGANISM: Homo sapiens
<220> FEATURE:
<221> NAME/KEY: CDS
<222> LOCATION: (92)..(2317)

<400> SEQUENCE: 1

```
ccgcctttaa cttctcggga agatgaggca gtttggcatc tgtggccgag ttgctgttgc      60
cgggtgatag ttggagcgga gacttagcat a atg gca gaa cct gtt tct cca         112
                                   Met Ala Glu Pro Val Ser Pro
                                    1               5 ctg aag cac ttt gtg ctg gct aag aag gcg att act gca atc ttt gac        160
Leu Lys His Phe Val Leu Ala Lys Lys Ala Ile Thr Ala Ile Phe Asp
         10                  15                  20 cag tta ctg gag ttt gtt act gaa gga tca cat ttt gtt gaa gca aca        208
Gln Leu Leu Glu Phe Val Thr Glu Gly Ser His Phe Val Glu Ala Thr
 25                  30                  35 tat aag aat ccg gaa ctt gat cga ata gcc act gaa gat gat ctg gta        256
Tyr Lys Asn Pro Glu Leu Asp Arg Ile Ala Thr Glu Asp Asp Leu Val
 40                  45                  50                  55 gaa atg caa gga tat aaa gac aag ctt tcc atc att ggt gag gtg cta        304
Glu Met Gln Gly Tyr Lys Asp Lys Leu Ser Ile Ile Gly Glu Val Leu
                 60                  65                  70 tct cgg aga cac atg aag gtg gca ttt ttt ggc agg aca agc agt ggg        352
Ser Arg Arg His Met Lys Val Ala Phe Phe Gly Arg Thr Ser Ser Gly
             75                  80                  85 aag agc tct gtt atc aat gca atg ttg tgg gat aaa gtt ctc cct agt        400
Lys Ser Ser Val Ile Asn Ala Met Leu Trp Asp Lys Val Leu Pro Ser
         90                  95                 100 ggg att ggc cat ata acc aat tgc ttc cta agt gtt gaa gga act gat        448
Gly Ile Gly His Ile Thr Asn Cys Phe Leu Ser Val Glu Gly Thr Asp
    105                 110                 115 gga gat aaa gcc tat ctt atg aca gaa gga tca gat gaa aaa aag agt        496
Gly Asp Lys Ala Tyr Leu Met Thr Glu Gly Ser Asp Glu Lys Lys Ser
120                 125                 130                 135 gtg aag aca gtt aat caa ctg gcc cat gcc ctt cac atg gac aaa gat        544
Val Lys Thr Val Asn Gln Leu Ala His Ala Leu His Met Asp Lys Asp
                140                 145                 150 ttg aaa gct ggc tgt ctt gta cgt gtg ttt tgc cca aaa gca aaa tgt        592
Leu Lys Ala Gly Cys Leu Val Arg Val Phe Cys Pro Lys Ala Lys Cys
            155                 160                 165
```

```
gcc ctc ttg aga gat gac ctg gtg tta gta gac agt cca ggc aca gat        640
Ala Leu Leu Arg Asp Asp Leu Val Leu Val Asp Ser Pro Gly Thr Asp
            170                 175                 180 gtc act aca gag ctg gat agc tgg att gat aag ttt tgc cta gat gct        688
Val Thr Thr Glu Leu Asp Ser Trp Ile Asp Lys Phe Cys Leu Asp Ala
        185                 190                 195 gat gtc ttt gtt ttg gtc gca aac tct gaa tca aca cta atg aat acg        736
Asp Val Phe Val Leu Val Ala Asn Ser Glu Ser Thr Leu Met Asn Thr
200                 205                 210                 215 gaa aaa cac ttt ttt cac aag gtg aat gag cgg ctt tcc aag cct aat        784
Glu Lys His Phe Phe His Lys Val Asn Glu Arg Leu Ser Lys Pro Asn
                220                 225                 230 att ttc att ctc aat aat cgt tgg gat gcc tct gca tca gaa cca gaa        832
Ile Phe Ile Leu Asn Asn Arg Trp Asp Ala Ser Ala Ser Glu Pro Glu
            235                 240                 245 tat atg gaa gac gta cgc aga cag cac atg gaa aga tgc ctg cat ttc        880
Tyr Met Glu Asp Val Arg Arg Gln His Met Glu Arg Cys Leu His Phe
        250                 255                 260 ttg gtg gag gag ctc aaa gtt gta aat gct tta gaa gca cag aat cgt        928
Leu Val Glu Glu Leu Lys Val Val Asn Ala Leu Glu Ala Gln Asn Arg
265                 270                 275 atc ttc ttt gtt tca gca aag gaa gtt ctt agt gct aga aag caa aaa        976
Ile Phe Phe Val Ser Ala Lys Glu Val Leu Ser Ala Arg Lys Gln Lys
280                 285                 290                 295 gca cag ggg atg cca gaa agt ggt gtg gca ctt gct gaa gga ttt cat       1024
Ala Gln Gly Met Pro Glu Ser Gly Val Ala Leu Ala Glu Gly Phe His
                300                 305                 310 gca aga tta cag gaa ttt cag aat ttt gaa caa atc ttt gag gag tgt       1072
Ala Arg Leu Gln Glu Phe Gln Asn Phe Glu Gln Ile Phe Glu Glu Cys
            315                 320                 325 atc tcg cag tca gca gtg aaa aca aag ttc gaa cag cac act atc aga       1120
Ile Ser Gln Ser Ala Val Lys Thr Lys Phe Glu Gln His Thr Ile Arg
        330                 335                 340 gct aaa cag ata cta gct act gtg aaa aac ata atg gat tca gta aac       1168
Ala Lys Gln Ile Leu Ala Thr Val Lys Asn Ile Met Asp Ser Val Asn
345                 350                 355 ctg gca gct gaa gat aaa agg cat tat tca gtg gaa gag agg gaa gac       1216
Leu Ala Ala Glu Asp Lys Arg His Tyr Ser Val Glu Glu Arg Glu Asp
360                 365                 370                 375 caa att gat aga ctg gac ttt att cga aac cag atg aac ctt tta aca       1264
Gln Ile Asp Arg Leu Asp Phe Ile Arg Asn Gln Met Asn Leu Leu Thr
                380                 385                 390 ctg gat gtt aag aaa aaa atc aag gag gtt acc gag gag gtg cca aac       1312
Leu Asp Val Lys Lys Lys Ile Lys Glu Val Thr Glu Glu Val Pro Asn
            395                 400                 405 aaa gtt tca tgt gca atg aca gat gaa att tgt cga ctg tct gtt ttg       1360
Lys Val Ser Cys Ala Met Thr Asp Glu Ile Cys Arg Leu Ser Val Leu
        410                 415                 420 gtt gat gaa ttt tgt tca gag ttt cat cct aat cca gat gta tta aaa       1408
Val Asp Glu Phe Cys Ser Glu Phe His Pro Asn Pro Asp Val Leu Lys
425                 430                 435 ata tat aaa agt gaa tta aat aag cac ata gag gat ggt atg gga aga       1456
Ile Tyr Lys Ser Glu Leu Asn Lys His Ile Glu Asp Gly Met Gly Arg
440                 445                 450                 455 aat ttg gct gat cga tgc acc gat gaa gta aac gcc tta gtg ctt cag       1504
Asn Leu Ala Asp Arg Cys Thr Asp Glu Val Asn Ala Leu Val Leu Gln
                460                 465                 470 acc cag caa gaa att att gaa aat ttg aag cca tta ctt cca gct ggt       1552
Thr Gln Gln Glu Ile Ile Glu Asn Leu Lys Pro Leu Leu Pro Ala Gly
```

-continued

|     |     |     |     | 475 |     |     |     |     | 480 |     |     |     |     | 485 |     |      |
|-----|-----|-----|-----|-----|-----|-----|-----|-----|-----|-----|-----|-----|-----|-----|-----|------|

```
ata cag gat aaa cta cat aca ctg atc cct tgc aag aaa ttt gat ctc   1600
Ile Gln Asp Lys Leu His Thr Leu Ile Pro Cys Lys Lys Phe Asp Leu
            490                 495                 500 agt tat aat cta aat tac cac aag tta tgt tca gat ttt caa gag gat   1648
Ser Tyr Asn Leu Asn Tyr His Lys Leu Cys Ser Asp Phe Gln Glu Asp
        505                 510                 515 att gta ttt cgt ttt tcc ctg ggc tgg tct tcc ctt gta cat cga ttt   1696
Ile Val Phe Arg Phe Ser Leu Gly Trp Ser Ser Leu Val His Arg Phe
520                 525                 530                 535 ttg ggc cct aga aat gct caa agg gtg ctc cta gga tta tca gag cct   1744
Leu Gly Pro Arg Asn Ala Gln Arg Val Leu Leu Gly Leu Ser Glu Pro
                540                 545                 550 atc ttt cag ctc cct aga tct tta gct tct act ccc act gct cct acc   1792
Ile Phe Gln Leu Pro Arg Ser Leu Ala Ser Thr Pro Thr Ala Pro Thr
            555                 560                 565 act cca gca acg cca gat aat gca tca cag gaa gaa ctc atg att aca   1840
Thr Pro Ala Thr Pro Asp Asn Ala Ser Gln Glu Glu Leu Met Ile Thr
        570                 575                 580 tta gta aca gga ttg gcg tcc gtt aca tct aga act tct atg ggc atc   1888
Leu Val Thr Gly Leu Ala Ser Val Thr Ser Arg Thr Ser Met Gly Ile
585                 590                 595 att att gtt gga gga gtg att tgg aaa act ata ggc tgg aaa ctc cta   1936
Ile Ile Val Gly Gly Val Ile Trp Lys Thr Ile Gly Trp Lys Leu Leu
600                 605                 610                 615 tct gtt tca tta act atg tat gga gct ttg tat ctt tat gaa aga ctg   1984
Ser Val Ser Leu Thr Met Tyr Gly Ala Leu Tyr Leu Tyr Glu Arg Leu
                620                 625                 630 agc tgg acc acc cat gcc aag gag cga gcc ttt aaa cag cag ttt gta   2032
Ser Trp Thr Thr His Ala Lys Glu Arg Ala Phe Lys Gln Gln Phe Val
            635                 640                 645 aac tat gca act gaa aaa ctg agg atg att gtt agc tcc acg agt gca   2080
Asn Tyr Ala Thr Glu Lys Leu Arg Met Ile Val Ser Ser Thr Ser Ala
        650                 655                 660 aac tgc agt cac caa gta aaa caa caa ata gct acc act ttt gct cgc   2128
Asn Cys Ser His Gln Val Lys Gln Gln Ile Ala Thr Thr Phe Ala Arg
665                 670                 675 ctg tgc caa caa gtt gat att acc cac aaa cag ctg gaa gaa gaa att   2176
Leu Cys Gln Gln Val Asp Ile Thr His Lys Gln Leu Glu Glu Glu Ile
680                 685                 690                 695 gct aga tta ccc aaa gaa ata gat cag ttg gag aaa atc caa aac aat   2224
Ala Arg Leu Pro Lys Glu Ile Asp Gln Leu Glu Lys Ile Gln Asn Asn
                700                 705                 710 tca aag ctc tta aga aat aaa gct gtt caa ctt gaa aat gag ctg gag   2272
Ser Lys Leu Leu Arg Asn Lys Ala Val Gln Leu Glu Asn Glu Leu Glu
            715                 720                 725 aat ttt act aag cag ttt cta cct tca agc aat gaa gaa tcc taa       2317
Asn Phe Thr Lys Gln Phe Leu Pro Ser Ser Asn Glu Glu Ser
        730                 735                 740 caatagagat tgctttggtg accatgatag gaggaaacga aacttgtaag attggaacag   2377
ttgttatttt tatgaaatta ctttaaatat gaattgtact atctgtacct aaatagcaaa   2437
gccctgtgta gattctggta atgatctgtc tcagggtatg tgtattttttg aagagtgtta   2497 tgtccttagt tttaattttg agtaaagaaa aggctaaaat catgaattag ttacaagcaa   2557
cagtaccaac ttatgtgacc cctgaggggt ggggctgtga gctcttaatt tgttttttgat   2617 tctgaaaaac tctgcttcct ggcatccagg agttagagat tgagcctttc atcttctttc   2677
tcaacactag tttttgatgc tttctttcat gggaatagtc acttttttat ttagtaaatc   2737
```
gcattgctgg aaccacc                                                    2754

<210> SEQ ID NO 2
<211> LENGTH: 741
<212> TYPE: PRT
<213> ORGANISM: Homo sapiens

<400> SEQUENCE: 2

```
Met Ala Glu Pro Val Ser Pro Leu Lys His Phe Val Leu Ala Lys Lys
 1               5                  10                  15

Ala Ile Thr Ala Ile Phe Asp Gln Leu Leu Glu Phe Val Thr Glu Gly
            20                  25                  30

Ser His Phe Val Glu Ala Thr Tyr Lys Asn Pro Glu Leu Asp Arg Ile
        35                  40                  45

Ala Thr Glu Asp Asp Leu Val Glu Met Gln Gly Tyr Lys Asp Lys Leu
    50                  55                  60

Ser Ile Ile Gly Glu Val Leu Ser Arg Arg His Met Lys Val Ala Phe
65                  70                  75                  80

Phe Gly Arg Thr Ser Ser Gly Lys Ser Val Ile Asn Ala Met Leu
                85                  90                  95

Trp Asp Lys Val Leu Pro Ser Gly Ile Gly His Ile Thr Asn Cys Phe
            100                 105                 110

Leu Ser Val Glu Gly Thr Asp Gly Asp Lys Ala Tyr Leu Met Thr Glu
        115                 120                 125

Gly Ser Asp Glu Lys Lys Ser Val Lys Thr Val Asn Gln Leu Ala His
    130                 135                 140

Ala Leu His Met Asp Lys Asp Leu Lys Ala Gly Cys Leu Val Arg Val
145                 150                 155                 160

Phe Cys Pro Lys Ala Lys Cys Ala Leu Leu Arg Asp Asp Leu Val Leu
                165                 170                 175

Val Asp Ser Pro Gly Thr Asp Val Thr Thr Glu Leu Asp Ser Trp Ile
            180                 185                 190

Asp Lys Phe Cys Leu Asp Ala Asp Val Phe Val Leu Val Ala Asn Ser
        195                 200                 205

Glu Ser Thr Leu Met Asn Thr Glu Lys His Phe Phe His Lys Val Asn
    210                 215                 220

Glu Arg Leu Ser Lys Pro Asn Ile Phe Ile Leu Asn Asn Arg Trp Asp
225                 230                 235                 240

Ala Ser Ala Ser Glu Pro Glu Tyr Met Glu Asp Val Arg Arg Gln His
                245                 250                 255

Met Glu Arg Cys Leu His Phe Leu Val Glu Glu Leu Lys Val Val Asn
            260                 265                 270

Ala Leu Glu Ala Gln Asn Arg Ile Phe Phe Val Ser Ala Lys Glu Val
        275                 280                 285

Leu Ser Ala Arg Lys Gln Lys Ala Gln Gly Met Pro Glu Ser Gly Val
    290                 295                 300

Ala Leu Ala Glu Gly Phe His Ala Arg Leu Gln Glu Phe Gln Asn Phe
305                 310                 315                 320

Glu Gln Ile Phe Glu Glu Cys Ile Ser Gln Ser Ala Val Lys Thr Lys
                325                 330                 335

Phe Glu Gln His Thr Ile Arg Ala Lys Gln Ile Leu Ala Thr Val Lys
            340                 345                 350

Asn Ile Met Asp Ser Val Asn Leu Ala Ala Glu Asp Lys Arg His Tyr
        355                 360                 365
```

```
Ser Val Glu Glu Arg Glu Asp Gln Ile Asp Arg Leu Asp Phe Ile Arg
    370                 375                 380
Asn Gln Met Asn Leu Leu Thr Leu Asp Val Lys Lys Ile Lys Glu
385                 390                 395                 400
Val Thr Glu Glu Val Pro Asn Lys Val Ser Cys Ala Met Thr Asp Glu
                405                 410                 415
Ile Cys Arg Leu Ser Val Leu Val Asp Glu Phe Cys Ser Glu Phe His
            420                 425                 430
Pro Asn Pro Asp Val Leu Lys Ile Tyr Lys Ser Glu Leu Asn Lys His
        435                 440                 445
Ile Glu Asp Gly Met Gly Arg Asn Leu Ala Asp Arg Cys Thr Asp Glu
    450                 455                 460
Val Asn Ala Leu Val Leu Gln Thr Gln Gln Glu Ile Ile Glu Asn Leu
465                 470                 475                 480
Lys Pro Leu Leu Pro Ala Gly Ile Gln Asp Lys Leu His Thr Leu Ile
                485                 490                 495
Pro Cys Lys Lys Phe Asp Leu Ser Tyr Asn Leu Asn Tyr His Lys Leu
            500                 505                 510
Cys Ser Asp Phe Gln Glu Asp Ile Val Phe Arg Phe Ser Leu Gly Trp
        515                 520                 525
Ser Ser Leu Val His Arg Phe Leu Gly Pro Arg Asn Ala Gln Arg Val
    530                 535                 540
Leu Leu Gly Leu Ser Glu Pro Ile Phe Gln Leu Pro Arg Ser Leu Ala
545                 550                 555                 560
Ser Thr Pro Thr Ala Pro Thr Thr Pro Ala Thr Pro Asp Asn Ala Ser
                565                 570                 575
Gln Glu Glu Leu Met Ile Thr Leu Val Thr Gly Leu Ala Ser Val Thr
            580                 585                 590
Ser Arg Thr Ser Met Gly Ile Ile Ile Val Gly Gly Val Ile Trp Lys
        595                 600                 605
Thr Ile Gly Trp Lys Leu Leu Ser Val Ser Leu Thr Met Tyr Gly Ala
    610                 615                 620
Leu Tyr Leu Tyr Glu Arg Leu Ser Trp Thr Thr His Ala Lys Glu Arg
625                 630                 635                 640
Ala Phe Lys Gln Gln Phe Val Asn Tyr Ala Thr Glu Lys Leu Arg Met
                645                 650                 655
Ile Val Ser Ser Thr Ser Ala Asn Cys Ser His Gln Val Lys Gln Gln
            660                 665                 670
Ile Ala Thr Thr Phe Ala Arg Leu Cys Gln Gln Val Asp Ile Thr His
        675                 680                 685
Lys Gln Leu Glu Glu Glu Ile Ala Arg Leu Pro Lys Glu Ile Asp Gln
    690                 695                 700
Leu Glu Lys Ile Gln Asn Asn Ser Lys Leu Leu Arg Asn Lys Ala Val
705                 710                 715                 720
Gln Leu Glu Asn Glu Leu Glu Asn Phe Thr Lys Gln Phe Leu Pro Ser
                725                 730                 735
Ser Asn Glu Glu Ser
            740

<210> SEQ ID NO 3
<211> LENGTH: 2754
<212> TYPE: DNA
<213> ORGANISM: Homo sapiens
<220> FEATURE:
```

```
<221> NAME/KEY: CDS
<222> LOCATION: (8)..(2317)

<400> SEQUENCE: 3 ttgatga atg tca ctg gtg tgt cat cag ttt gca tgt cta tca tcc act       49
        Met Ser Leu Val Cys His Gln Phe Ala Cys Leu Ser Ser Thr
        1               5                   10 tta gtt ggt gct ttt cta act tta tct ccc tct agt agc ata atg gca       97
Leu Val Gly Ala Phe Leu Thr Leu Ser Pro Ser Ser Ser Ile Met Ala
15                  20                  25                  30 gaa cct gtt tct cca ctg aag cac ttt gtg ctg gct aag aag gcg att      145
Glu Pro Val Ser Pro Leu Lys His Phe Val Leu Ala Lys Lys Ala Ile
                35                  40                  45 act gca atc ttt gac cag tta ctg gag ttt gtt act gaa gga tca cat      193
Thr Ala Ile Phe Asp Gln Leu Leu Glu Phe Val Thr Glu Gly Ser His
            50                  55                  60 ttt gtt gaa gca aca tat aag aat ccg gaa ctt gat cga ata gcc act      241
Phe Val Glu Ala Thr Tyr Lys Asn Pro Glu Leu Asp Arg Ile Ala Thr
65                  70                  75 gaa gat gat ctg gta gaa atg caa gga tat aaa gac aag ctt tcc atc      289
Glu Asp Asp Leu Val Glu Met Gln Gly Tyr Lys Asp Lys Leu Ser Ile
80                  85                  90 att ggt gag gtg cta tct cgg aga cac atg aag gtg gca ttt ttt ggc      337
Ile Gly Glu Val Leu Ser Arg Arg His Met Lys Val Ala Phe Phe Gly
95                  100                 105                 110 agg aca agc agt ggg aag agc tct gtt atc aat gca atg ttg tgg gat      385
Arg Thr Ser Ser Gly Lys Ser Ser Val Ile Asn Ala Met Leu Trp Asp
                115                 120                 125 aaa gtt ctc cct agt ggg att ggc cat ata acc aat tgc ttc cta agt      433
Lys Val Leu Pro Ser Gly Ile Gly His Ile Thr Asn Cys Phe Leu Ser
            130                 135                 140 gtt gaa gga act gat gga gat aaa gcc tat ctt atg aca gaa gga tca      481
Val Glu Gly Thr Asp Gly Asp Lys Ala Tyr Leu Met Thr Glu Gly Ser
        145                 150                 155 gat gaa aaa aag agt gtg aag aca gtt aat caa ctg gcc cat gcc ctt      529
Asp Glu Lys Lys Ser Val Lys Thr Val Asn Gln Leu Ala His Ala Leu
160                 165                 170 cac atg gac aaa gat ttg aaa gct ggc tgt ctt gta cgt gtg ttt tgc      577
His Met Asp Lys Asp Leu Lys Ala Gly Cys Leu Val Arg Val Phe Cys
175                 180                 185                 190 cca aaa gca aaa tgt gcc ctc ttg aga gat gac ctg gtg tta gta gac      625
Pro Lys Ala Lys Cys Ala Leu Leu Arg Asp Asp Leu Val Leu Val Asp
                195                 200                 205 agt cca ggc aca gat gtc act aca gag ctg gat agc tgg att gat aag      673
Ser Pro Gly Thr Asp Val Thr Thr Glu Leu Asp Ser Trp Ile Asp Lys
            210                 215                 220 ttt tgc cta gat gct gat gtc ttt gtt ttg gtc gca aac tct gaa tca      721
Phe Cys Leu Asp Ala Asp Val Phe Val Leu Val Ala Asn Ser Glu Ser
        225                 230                 235 aca cta atg aat acg gaa aaa cac ttt ttt cac aag gtg aat gag cgg      769
Thr Leu Met Asn Thr Glu Lys His Phe Phe His Lys Val Asn Glu Arg
240                 245                 250 ctt tcc aag cct aat att ttc att ctc aat aat cgt tgg gat gcc tct      817
Leu Ser Lys Pro Asn Ile Phe Ile Leu Asn Asn Arg Trp Asp Ala Ser
255                 260                 265                 270 gca tca gaa cca gaa tat atg gaa gac gta cgc aga cag cac atg gaa      865
Ala Ser Glu Pro Glu Tyr Met Glu Asp Val Arg Arg Gln His Met Glu
                275                 280                 285 aga tgc ctg cat ttc ttg gtg gag gag ctc aaa gtt gta aat gct tta      913
Arg Cys Leu His Phe Leu Val Glu Glu Leu Lys Val Val Asn Ala Leu
```

```
                        -continued
          290                 295                 300
gaa gca cag aat cgt atc ttc ttt gtt tca gca aag gaa gtt ctt agt    961
Glu Ala Gln Asn Arg Ile Phe Phe Val Ser Ala Lys Glu Val Leu Ser
        305                 310                 315 gct aga aag caa aaa gca cag ggg atg cca gaa agt ggt gtg gca ctt   1009
Ala Arg Lys Gln Lys Ala Gln Gly Met Pro Glu Ser Gly Val Ala Leu
320                 325                 330 gct gaa gga ttt cat gca aga tta cag gaa ttt cag aat ttt gaa caa   1057
Ala Glu Gly Phe His Ala Arg Leu Gln Glu Phe Gln Asn Phe Glu Gln
335                 340                 345                 350 atc ttt gag gag tgt atc tcg cag tca gca gtg aaa aca aag ttc gaa   1105
Ile Phe Glu Glu Cys Ile Ser Gln Ser Ala Val Lys Thr Lys Phe Glu
            355                 360                 365 cag cac act atc aga gct aaa cag ata cta gct act gtg aaa aac ata   1153
Gln His Thr Ile Arg Ala Lys Gln Ile Leu Ala Thr Val Lys Asn Ile
        370                 375                 380 atg gat tca gta aac ctg gca gct gaa gat aaa agg cat tat tca gtg   1201
Met Asp Ser Val Asn Leu Ala Ala Glu Asp Lys Arg His Tyr Ser Val
    385                 390                 395 gaa gag agg gaa gac caa att gat aga ctg gac ttt att cga aac cag   1249
Glu Glu Arg Glu Asp Gln Ile Asp Arg Leu Asp Phe Ile Arg Asn Gln
400                 405                 410 atg aac ctt tta aca ctg gat gtt aag aaa aaa atc aag gag gtt acc   1297
Met Asn Leu Leu Thr Leu Asp Val Lys Lys Lys Ile Lys Glu Val Thr
415                 420                 425                 430 gag gag gtg cca aac aaa gtt tca tgt gca atg aca gat gaa att tgt   1345
Glu Glu Val Pro Asn Lys Val Ser Cys Ala Met Thr Asp Glu Ile Cys
            435                 440                 445 cga ctg tct gtt ttg gtt gat gaa ttt tgt tca gag ttt cat cct aat   1393
Arg Leu Ser Val Leu Val Asp Glu Phe Cys Ser Glu Phe His Pro Asn
        450                 455                 460 cca gat gta tta aaa ata tat aaa agt gaa tta aat aag cac ata gag   1441
Pro Asp Val Leu Lys Ile Tyr Lys Ser Glu Leu Asn Lys His Ile Glu
    465                 470                 475 gat ggt atg gga aga aat ttg gct gat cga tgc acc gat gaa gta aac   1489
Asp Gly Met Gly Arg Asn Leu Ala Asp Arg Cys Thr Asp Glu Val Asn
480                 485                 490 gcc tta gtg ctt cag acc cag caa gaa att att gaa aat ttg aag cca   1537
Ala Leu Val Leu Gln Thr Gln Gln Glu Ile Ile Glu Asn Leu Lys Pro
495                 500                 505                 510 tta ctt cca gct ggt ata cag gat aaa cta cat aca ctg atc cct tgc   1585
Leu Leu Pro Ala Gly Ile Gln Asp Lys Leu His Thr Leu Ile Pro Cys
            515                 520                 525 aag aaa ttt gat ctc agt tat aat cta aat tac cac aag tta tgt tca   1633
Lys Lys Phe Asp Leu Ser Tyr Asn Leu Asn Tyr His Lys Leu Cys Ser
        530                 535                 540 gat ttt caa gag gat att gta ttt cgt ttt tcc ctg ggc tgg tct tcc   1681
Asp Phe Gln Glu Asp Ile Val Phe Arg Phe Ser Leu Gly Trp Ser Ser
    545                 550                 555 ctt gta cat cga ttt ttg ggc cct aga aat gct caa agg gtg ctc cta   1729
Leu Val His Arg Phe Leu Gly Pro Arg Asn Ala Gln Arg Val Leu Leu
560                 565                 570 gga tta tca gag cct atc ttt cag ctc cct aga tct tta gct tct act   1777
Gly Leu Ser Glu Pro Ile Phe Gln Leu Pro Arg Ser Leu Ala Ser Thr
575                 580                 585                 590 ccc act gct cct acc act cca gca acg cca gat aat gca tca cag gaa   1825
Pro Thr Ala Pro Thr Thr Pro Ala Thr Pro Asp Asn Ala Ser Gln Glu
            595                 600                 605 gaa ctc atg att aca tta gta aca gga ttg gcg tcc gtt aca tct aga   1873
Glu Leu Met Ile Thr Leu Val Thr Gly Leu Ala Ser Val Thr Ser Arg
```

```
                Glu Leu Met Ile Thr Leu Val Thr Gly Leu Ala Ser Val Thr Ser Arg
                        610                 615                 620 act tct atg ggc atc att att gtt gga gga gtg att tgg aaa act ata      1921
Thr Ser Met Gly Ile Ile Ile Val Gly Gly Val Ile Trp Lys Thr Ile
            625                 630                 635 ggc tgg aaa ctc cta tct gtt tca tta act atg tat gga gct ttg tat      1969
Gly Trp Lys Leu Leu Ser Val Ser Leu Thr Met Tyr Gly Ala Leu Tyr
640                 645                 650 ctt tat gaa aga ctg agc tgg acc acc cat gcc aag gag cga gcc ttt      2017
Leu Tyr Glu Arg Leu Ser Trp Thr Thr His Ala Lys Glu Arg Ala Phe
655                 660                 665                 670 aaa cag cag ttt gta aac tat gca act gaa aaa ctg agg atg att gtt      2065
Lys Gln Gln Phe Val Asn Tyr Ala Thr Glu Lys Leu Arg Met Ile Val
                675                 680                 685 agc tcc acg agt gca aac tgc agt cac caa gta aaa caa caa ata gct      2113
Ser Ser Thr Ser Ala Asn Cys Ser His Gln Val Lys Gln Gln Ile Ala
            690                 695                 700 acc act ttt gct cgc ctg tgc caa caa gtt gat att acc cac aaa cag      2161
Thr Thr Phe Ala Arg Leu Cys Gln Gln Val Asp Ile Thr His Lys Gln
        705                 710                 715 ctg gaa gaa gaa att gct aga tta ccc aaa gaa ata gat cag ttg gag      2209
Leu Glu Glu Glu Ile Ala Arg Leu Pro Lys Glu Ile Asp Gln Leu Glu
    720                 725                 730 aaa atc caa aac aat tca aag ctc tta aga aat aaa gct gtt caa ctt      2257
Lys Ile Gln Asn Asn Ser Lys Leu Leu Arg Asn Lys Ala Val Gln Leu
735                 740                 745                 750 gaa aat gag ctg gag aat ttt act aag cag ttt cta cct tca agc aat      2305
Glu Asn Glu Leu Glu Asn Phe Thr Lys Gln Phe Leu Pro Ser Ser Asn
                755                 760                 765 gaa gaa tcc taa caatagagat tgctttggtg accatgatag gaggaaacga          2357
Glu Glu Ser aacttgtaag attggaacag ttgttatttt tatgaaatta ctttaaatat gaattgtact    2417
atctgtacct aaatagcaaa gccctgtgta gattctggta atgatctgtc tcagggtatg    2477 tgtattttg aagagtgtta tgtccttagt tttaattttg agtaaagaaa aggctaaaat     2537
catgaattag ttacaagcaa cagtaccaac ttatgtgacc cctgaggggt ggggctgtga    2597
gctcttaatt tgttttttgat tctgaaaaac tctgcttcct ggcatccagg agttagagat   2657
tgagcctttc atcttctttc tcaacactag ttttttgatgc tttctttcat gggaatagtc   2717
acttttttat ttagtaaatc gcattgctgg aaccacc                             2754

<210> SEQ ID NO 4
<211> LENGTH: 769
<212> TYPE: PRT
<213> ORGANISM: Homo sapiens

<400> SEQUENCE: 4

Met Ser Leu Val Cys His Gln Phe Ala Cys Leu Ser Ser Thr Leu Val
1               5                   10                  15

Gly Ala Phe Leu Thr Leu Ser Pro Ser Ser Ile Met Ala Glu Pro
            20                  25                  30

Val Ser Pro Leu Lys His Phe Val Leu Ala Lys Lys Ala Ile Thr Ala
        35                  40                  45

Ile Phe Asp Gln Leu Leu Glu Phe Val Thr Glu Gly Ser His Phe Val
    50                  55                  60

Glu Ala Thr Tyr Lys Asn Pro Glu Leu Asp Arg Ile Ala Thr Glu Asp
65                  70                  75                  80
```

-continued

```
Asp Leu Val Glu Met Gln Gly Tyr Lys Asp Lys Leu Ser Ile Ile Gly
                 85                  90                  95

Glu Val Leu Ser Arg Arg His Met Lys Val Ala Phe Phe Gly Arg Thr
            100                 105                 110

Ser Ser Gly Lys Ser Ser Val Ile Asn Ala Met Leu Trp Asp Lys Val
        115                 120                 125

Leu Pro Ser Gly Ile Gly His Ile Thr Asn Cys Phe Leu Ser Val Glu
    130                 135                 140

Gly Thr Asp Gly Asp Lys Ala Tyr Leu Met Thr Glu Gly Ser Asp Glu
145                 150                 155                 160

Lys Lys Ser Val Lys Thr Val Asn Gln Leu Ala His Ala Leu His Met
                165                 170                 175

Asp Lys Asp Leu Lys Ala Gly Cys Leu Val Arg Val Phe Cys Pro Lys
            180                 185                 190

Ala Lys Cys Ala Leu Leu Arg Asp Asp Leu Val Leu Val Asp Ser Pro
        195                 200                 205

Gly Thr Asp Val Thr Thr Glu Leu Asp Ser Trp Ile Asp Lys Phe Cys
    210                 215                 220

Leu Asp Ala Asp Val Phe Val Leu Val Ala Asn Ser Glu Ser Thr Leu
225                 230                 235                 240

Met Asn Thr Glu Lys His Phe Phe His Lys Val Asn Glu Arg Leu Ser
                245                 250                 255

Lys Pro Asn Ile Phe Ile Leu Asn Asn Arg Trp Asp Ala Ser Ala Ser
            260                 265                 270

Glu Pro Glu Tyr Met Glu Asp Val Arg Arg Gln His Met Glu Arg Cys
        275                 280                 285

Leu His Phe Leu Val Glu Leu Lys Val Val Asn Ala Leu Glu Ala
    290                 295                 300

Gln Asn Arg Ile Phe Phe Val Ser Ala Lys Glu Val Leu Ser Ala Arg
305                 310                 315                 320

Lys Gln Lys Ala Gln Gly Met Pro Glu Ser Gly Val Ala Leu Ala Glu
                325                 330                 335

Gly Phe His Ala Arg Leu Gln Glu Phe Gln Asn Phe Glu Gln Ile Phe
            340                 345                 350

Glu Glu Cys Ile Ser Gln Ser Ala Val Lys Thr Lys Phe Glu Gln His
        355                 360                 365

Thr Ile Arg Ala Lys Gln Ile Leu Ala Thr Val Lys Asn Ile Met Asp
    370                 375                 380

Ser Val Asn Leu Ala Ala Glu Asp Lys Arg His Tyr Ser Val Glu Glu
385                 390                 395                 400

Arg Glu Asp Gln Ile Asp Arg Leu Asp Phe Ile Arg Asn Gln Met Asn
                405                 410                 415

Leu Leu Thr Leu Asp Val Lys Lys Lys Ile Lys Glu Val Thr Glu Glu
            420                 425                 430

Val Pro Asn Lys Val Ser Cys Ala Met Thr Asp Glu Ile Cys Arg Leu
        435                 440                 445

Ser Val Leu Val Asp Glu Phe Cys Ser Glu Phe His Pro Asn Pro Asp
    450                 455                 460

Val Leu Lys Ile Tyr Lys Ser Glu Leu Asn Lys His Ile Glu Asp Gly
465                 470                 475                 480

Met Gly Arg Asn Leu Ala Asp Arg Cys Thr Asp Glu Val Asn Ala Leu
                485                 490                 495

Val Leu Gln Thr Gln Gln Glu Ile Ile Glu Asn Leu Lys Pro Leu Leu
```

-continued

```
                500                 505                 510
Pro Ala Gly Ile Gln Asp Lys Leu His Thr Leu Ile Pro Cys Lys Lys
        515                 520                 525

Phe Asp Leu Ser Tyr Asn Leu Asn Tyr His Lys Leu Cys Ser Asp Phe
        530                 535                 540

Gln Glu Asp Ile Val Phe Arg Phe Ser Leu Gly Trp Ser Ser Leu Val
545                 550                 555                 560

His Arg Phe Leu Gly Pro Arg Asn Ala Gln Arg Val Leu Leu Gly Leu
                565                 570                 575

Ser Glu Pro Ile Phe Gln Leu Pro Arg Ser Leu Ala Ser Thr Pro Thr
        580                 585                 590

Ala Pro Thr Thr Pro Ala Thr Pro Asp Asn Ala Ser Gln Glu Glu Leu
        595                 600                 605

Met Ile Thr Leu Val Thr Gly Leu Ala Ser Val Thr Ser Arg Thr Ser
        610                 615                 620

Met Gly Ile Ile Ile Val Gly Gly Val Ile Trp Lys Thr Ile Gly Trp
625                 630                 635                 640

Lys Leu Leu Ser Val Ser Leu Thr Met Tyr Gly Ala Leu Tyr Leu Tyr
                645                 650                 655

Glu Arg Leu Ser Trp Thr Thr His Ala Lys Glu Arg Ala Phe Lys Gln
                660                 665                 670

Gln Phe Val Asn Tyr Ala Thr Glu Lys Leu Arg Met Ile Val Ser Ser
                675                 680                 685

Thr Ser Ala Asn Cys Ser His Gln Val Lys Gln Ile Ala Thr Thr
        690                 695                 700

Phe Ala Arg Leu Cys Gln Gln Val Asp Ile Thr His Lys Gln Leu Glu
705                 710                 715                 720

Glu Glu Ile Ala Arg Leu Pro Lys Glu Ile Asp Gln Leu Glu Lys Ile
                725                 730                 735

Gln Asn Asn Ser Lys Leu Leu Arg Asn Lys Ala Val Gln Leu Glu Asn
                740                 745                 750

Glu Leu Glu Asn Phe Thr Lys Gln Phe Leu Pro Ser Ser Asn Glu Glu
        755                 760                 765

Ser
```

HUMAN MITOCHONDRIAL PROTEINS AND POLYNUCLEOTIDE ENCODING THE PROTEINS

This application is a divisional of application Ser. No. 10/470,554, filed Oct. 20, 2003, now U.S. Pat. No. 7,026,452, which is a 371 national stage application of PCT/JP01/09783, filed Nov. 8, 2001. The teachings of the above-referenced applications are herein incorporated by reference.

TECHNICAL FIELD

The invention of the present application relates to proteins derived from human mitochondria, polynucleotide encoding such proteins, and antibodies against such proteins. More specifically, the invention of the present application relates to NOVEL HUMAN PROTEINS AND ANTIBODIES which are useful for diagnosis and treatment of a variety of diseases caused by mutation of mitochondrial DNA. The invention also relates to POLYNUCLEOTIDES which are useful as probes for gene diagnosis of the above diseases, gene sources for gene therapy, and gene sources for mass production of the proteins according to the present invention. The invention further relates to LIPOSOMES (LIPOSOME VECTORS) which enable mitochondria-specific transfer of foreign genes or drugs.

BACKGROUND ART

Mitochondria are organelles each composed of an outer membrane and an inner membrane having a cristae structure, and are distributed throughout cytoplasm in a tubular reticular structure. Mitochondria also have their own genes (mitochondrial DNA) besides nuclear genes.

Mitochondria have the functions of, for example, producing energy which is necessary for activity of cells, and catalyzing biosynthesis and degradation of crucial biological substances. Mitochondria are also involved in other biological activities such as production of active oxygen and production of apoptosis-inducing signal.

Mitochondria dynamically change their forms by migration, fusion and disintegration in response to environmental changes in the cell. In particular, under the pathological conditions, such as the case of liver disease, congenital muscular dystrophy, gastric cancer, myeloma, and dilated cardiomyopathy due to abnormality of mitochondrial DNA, mitochondria significantly change their forms and distributions, and express megamitochondria, annular or axle form, or morphological and structural variations having an annular or concentric cristae structure.

As a mammalian gene in relation to these mitochondria, a gene involved in disintegration of mitochondria is known (J. Cell Biol. 143: 351-358, 1998). On the other hand, as a gene involved in fusion of mitochondria, a gene product Fzo expressed at the time of formation of sperm of drosophila, which promotes mitochondrial fusion (Cell 90: 121-129, 1997), and a gene product Fzo1p which promotes fusion of mitochondria occurring at the time of meiotic division of fission yeast (J. Cell Biol. 143: 359-373, 1998) are known. However, mammalian genes involved in fusion of mitochondria have not been identified.

Examples of the diseases caused by mutation of mitochondrial DNA include mitochondrial myopathy, cardiomyopathy, type II diabetes, Alzheimer's disease, Parkinson's disease and the like. Such a mutant mitochondrial DNA exists within a cell in the state of heteroplasmy wherein mutant mitochondrial DNA and normal mitochondrial DNA coexist. When the existing ratio of mutant DNA exceeds a predetermined threshold, the cell function deteriorates to lead appearance of disease symptoms. Gene therapeutic methods against these diseases have not been established because, unlike nuclear DNA, mitochondrial DNA exists in mitochondria. As a method which enables gene therapy targeted towards mitochondrial DNA, transfers of foreign mitochondria by means of cybrid method or microinjection (J. Cell Biol. 67: 174-188, 1975, Cell 52: 811-819, 1988) have been reported heretofore. However, these methods entail the drawbacks that large amounts of cytoplasm components other than mitochondria are introduced, and that desired genes and substances cannot be introduced into mitochondria. Therefore, they are far from actual use at present.

As described above, mitochondria changes their forms in accordance with the pathological condition of particular disease, and a protein promoting aggregation and fusion of mitochondria is thought to be involved in such a morphological change. Therefore, it is expected that isolation of human proteins as described above and detailed analysis of their functions will open new avenues for clarifying causes of mitochondrial diseases in human and developing preventive and therapeutic methods thereof. Moreover, it is expected that antibodies against such proteins and probes derived from genes encoding such proteins will be useful materials for diagnosing conditions of mitochondria in a particular disease.

Furthermore, protein samples which promote aggregation or fusion of mitochondria are expected to provide new measures for specific transfer of foreign genes and drugs targeted on mitochondria.

DISCLOSURE OF INVENTION

It is an object of the invention of the present application to provide novel human proteins which promote aggregation or fusion of mitochondria, and polynucleotides encoding such proteins.

It is also an object of the invention of the present application to provide antibodies against the proteins, and proteoliposomes which contain such protein as an active ingredient.

In order to achieve the above objects, the present application provides the following inventions (1) to (8).
(1) An isolated and purified human mitochondrial protein comprising the amino acid sequence of SEQ ID NO: 2 or SEQ ID NO: 4.
(2) A polynucleotide encoding the protein of the invention (1).
(3) The polynucleotide of the invention (2), which comprises the base sequence for the protein translation region in SEQ ID NO: 1 or SEQ ID NO: 3.
(4) A polynucleotide with which a polynucleotide having the sequence of SEQ ID NO: 1 or SEQ ID NO: 3 or a part thereof hybridizes under a stringent condition.
(5) An expression vector, which expresses the polynucleotide of the invention (3) in the in vitro translating system or in a host cell.
(6) A transformant with the expression vector of the invention (5), which produces the human mitochondrial protein of the invention (1).
(7) An antibody against the human mitochondrial protein of the invention (1).
(8) A proteoliposome composed of the human mitochondrial protein of the invention (1) and lipid.

BEST MODE FOR CARRYING OUT THE INVENTION

The protein according to the invention (1) refers to two kinds of isolated and purified human proteins respectively having amino acid sequences of SEQ ID NO: 2 and SEQ ID NO: 4 (hereinafter, referred to as "Hfzo1 protein" and "Hfzo2 protein", respectively, or "Hfzo proteins" for both). Each of these proteins coded by nuclear genome is expressed at nucleus, migrates toward mitochondrial membrane to localize there, and thereby functions to promote aggregation and induction of mitochondria. To be more specific, these proteins localized at different mitochondrial membranes are bound with each other, whereby aggregation and fusion among mitochondria are achieved. These proteins are the proteins that are first characterized in mammal. These proteins have coiled-coiled domains, a GTPase domain and transmembrane domains in their primary structure, so that similarity with the primary structure of a device (SNARE, rab, syntaxin or the like) involved in fusion of vesicle is found.

These Hfzo proteins according to the invention (1) can be obtained, for example, by isolating from mitochondria of human cell, by preparing a peptide by way of chemical synthesis based the amino acid sequence of SEQ ID NO: 2 or SEQ ID NO: 4, or by producing by recombinant DNA technique using a polynucleotide encoding the amino acid sequence of SEQ ID NO: 2 or SEQ ID NO: 4. Among these, the method based on the recombinant DNA technique is preferably used. For example, by preparing an RNA from a vector harboring the polynucleotide (ORF region of cDNA) according to the invention (3) by in vitro transcription, followed by in vitro translation with the use of this RNA as a template, it is possible to achieve in vitro expression of protein. In addition, by recombining the polynucleotide into an appropriate expression vector using known methods, it is possible to express the protein encoded by the polynucleotide on a large scale in prokaryotic cells such as *Escherichia coli* and *Bacillus subtilis*, or in eukaryotic cells such as yeast, insect cells and mammalian cells.

In the case of expressing DNA by in vitro translation and producing the Hfzo protein according to the invention (1), the polynucleotide according to the invention (3) is inserted into a vector having an RNA polymerase promoter to construct a recombinant vector (invention (5)). Then this vector is added to an in vitro translation system such as rabbit reticulocyte lysate or wheat germ extract containing an RNA polymerase corresponding to the promoter, whereby the protein according to the invention (1) is produced in vitro. Examples of the RNA polymerase promoter include T7, T3 and SP6. Examples of vectors containing these RNA polymerase promoters include pCMV-SPORT, pKA1, pCDM8, pT3/T7 18, pT7/3 19 and pBluescript II.

In the case of expressing DNA in a microorganism such as *Escherichia coli* to produce the Hfzo protein according to the invention (1), the polynucleotide according to the invention (3) is recombined into an expression vector which is replicable in a microorganism and having an origin, promoter, ribosome binding site, DNA cloning site, terminator and the like, to thereby create an expression vector (invention (5)). Then a host cell is transformed with this expression vector, and the resultant transformant (invention (6)) is cultured. In this manner, a protein encoded by the present polynucleotide can be produced in the microorganism on a large scale. In this case, by expressing DNA in which an initiation codon and a stop codon are added before and after a given translation region, it is possible to obtain a protein fragment including the given region. Alternatively, it may be expressed in the form of a fusion protein with other protein. By cutting this fusion protein with an appropriate protease, it is possible to acquire only a protein portion encoded by the present polynucleotide. Examples of expression vector to be used for *Escherichia coli* include pUC series, pBluescript II, pET expression system, pGEX expression system, pQE expression system and the like.

In the case of expressing DNA in an eukaryotic cell to produce the Hfzo protein according to the invention (1), the polynucleotide according to the invention (3) is inserted into an expression vector for eukaryotic cell having a promoter, splicing regions, poly(A) addition site and the like to create a recombinant vector (invention (5)), and then the recombinant vector is introduced into an eukaryotic cell (invention (6)). In this manner the protein according to the invention (1) can be produced in a eukaryotic cell. Examples of the expression vector include pKA1, pCDM8, pSVK3, pMSG, pSVL, pBKCMV, pBK-RSV, EBV vector, pRS, pYES2 and the like. By using pIND/V5-His, pFLAG-CMV-2, pEGFP-N1, pEGFP-C1 and the like as an expression vector, it is possible to express fusion proteins to which various tags such as His tag, FLAG tag, GFP and the like are added. As the eukaryotic cell, mammalian culture cells such as simian kidney cell COS7 and Chinese hamster ovarian cell CHO, *Saccharomyces cerevisiae, Schizosaccharomyces pombe*, silkworm cell, platanna egg cell are commonly used, however, any eukaryotic cells can be used insofar as they can express the protein according to the invention (1). For introducing the expression vector into the eukaryotic cell, known methods such as electroporation, calcium phosphate method, liposome method and DEAE-dextran method can be used.

For isolating and purifying an objective protein from the culture following expression the Hfzo protein according to the invention (1) in a prokaryotic or eukaryotic cell, known separating operations are used in combination. Examples of such operations include treatment with denaturant such as urea or with surfactant, ultrasonic treatment, enzyme digestion, salt precipitation or solvent precipitation method, dialysis, centrifugation, ultrafiltration, gel filtration, SDS-PAGE, isoelectric focusing, ion-exchange chromatography, hydrophobicity chromatography, affinity chromatography, reverse-phase chromatography and the like.

The Hfzo protein according to the invention (1) implies peptide fragments (of 5 or more amino acid resides) comprising any partial amino acid sequences of the amino acid sequence represented by SEQ ID NO: 2 or SEQ ID NO: 4. These peptide fragments can be used as antigens for preparing antibodies. Furthermore, the protein according to the invention (1) implies fusion proteins with other arbitrary proteins. For example, fusion proteins with glutathione-S-transferase (GST) or green fluorescent protein (GFP) can be exemplified. Furthermore, the protein according to the invention (1) possibly undergoes various modifications in a cell after translation. Therefore, proteins resulting from such modifications also fall within the bound of the protein according to the invention (1). Examples of such post-translational modification include leaving of N-terminal methionine, N-terminal acetylation, addition of sugar chain, restrictive lysis by intracellular protease, myristoylation, isoprenylation, phosphorylation, and the like.

The invention (2) provides a polynucleotide encoding the protein of the invention (1), and implies human nuclear DNA (genomic DNA), mRNA and cDNA thereof (concretely, polynucleotides having base sequences represented by SEQ ID NO: 1 and SEQ ID NO: 3, respectively), and complementary strands thereof.

The polynucleotide of the invention (3) refers to two kinds of cDNAs comprising a base sequence which constitutes the translation region (open reading frame: ORF) of SEQ ID NO: 1 or SEQ ID NO: 3. Since the protein of the invention (1) is expressed in any cells, by screening human cDNA library constructed from human cells with the use of oligonucleotide probes synthesized on the basis of the base sequence of SEQ ID NO: 1 or SEQ ID NO: 3, it is possible to readily acquire the same clone as the polynucleotide of the invention (3). cDNA is synthesized by using poly(A)+ RNA extracted from human cells as a template. The human cells may be those surgically removed from human body or culture cells. cDNA can be synthesized by using known methods (Okayama, H. and Berg, P., (1982) Mol. Cell Biol. 2, 161-170; Gubler, U. and Hoffman, (1983) J. Gene 25, 263-269; Kato, S. et al. (1994) Gene, 150, 243-250). Alternatively, objective cDNA may be synthesized by an RT-PCR method using these poligonucleotides as primers and an mRNA isolated from human cell as a template.

In general, polymorphism due to individual specificity is often observed in human genes. Therefore, polynucleotides wherein addition or deletion of one or more nucleotide(s) and/or substitution with other nucleotide(s) is made in the base sequence of SEQ ID NO: 1 or SEQ ID NO: 3 also fall within the bound of the polynucleotide according to the invention (3).

Similarly, proteins wherein addition or deletion of one or more amino acid(s) generated due to these alteration and/or substitution with other amino acid(s) is made also fall within the bound of the protein according to the invention (1) insofar as the have Hfzo protein activity.

Furthermore, the polynucleotide according to the invention (3) implies DNA fragments (10 bp or more) comprising any partial base sequences of the base sequence of SEQ ID NO: 1 or SEQ ID NO: 3. Also, DNA fragments made up of a sense strand and an antisense strand fall within this bound. These DNA fragments can be used as probes for gene diagnosis.

The invention (4) provides a polynucleotide to which a polynucleotide comprising a sequence represented by SEQ ID NO: 1 or SEQ ID NO: 3 or a partial continuous sequence thereof will hybridize in a stringent condition, and implies partial regions of nuclear DNA of all mammals including human (DNA fragments), as well as mRNAs and cDNAs thereof. Herein, the term "stringent condition" refers to a condition that allows selective and detectable specific connection between a polynucleotide comprising a base sequence of SEQ ID NO: 1 or SEQ ID NO: 3 or a partial continuous sequence thereof (for example 10 bp or more) and nuclear DNA. The stringent condition is defined by salt concentration, organic solvent (for example, formamide), temperature and other known conditions. That is, stringency is increased by reducing the salt concentration, by increasing the concentration or organic solvent or by elevating the hybridization temperature. For example, the stringent salt concentration is usually about 750 mM or less of NaCl and about 75 mM or less of sodium triphosphate, more preferably about 500 mM or less of NaCl and about 50 mM or less of sodium triphosphate, and most preferably about 250 mM or less of NaCl and about 25 mM or less of sodium triphosphate. The stringent concentration of organic solvent is about 35% or more, and most preferably about 50% or more in the case of formamide. The stringent temperature condition is about 30° C. or more, more preferably about 37° C. or more, and most preferably about 42° C. or more. Examples of other conditions include hybridization time, concentration of washing agent (for example, SDS) and presence/absence of carrier DNA, and combinations of these conditions will provide various stringencies. Also the condition of washing after hybridization will influence on the stringency. This washing condition is also defined by salt concentration and temperature, the less the salt concentration and the higher the temperature, the more the stringency of washing. For example, the stringent salt condition for washing is preferably about 30 mM or less of NaCl and about 3 mM or less of sodium triphosphate, more preferably about 15 mM or less of NaCl and about 1.5 mM or less of sodium triphosphate. The stringent temperature condition for washing is about 25° C. or more, more preferably about 42° C. or more, and most preferably about 68° C. or more. The mitochondrial DNA fragment according to the invention (4) can be isolated by screening a genome library prepared from human nuclear DNA through hybridization and washing treatment under stringent conditions as described above using the aforementioned polynucleotide as a probe.

The polynucleotide (genomic DNA fragment) of the present invention (4) includes expression regulating regions (promoter/enhancer, suppresser sequences or the like) with respect to the Hfzo protein coding region. These expression regulating sequences are useful as materials for screening substances which regulate in vivo expression of the Hfzo protein.

The antibody according to the invention (7) can be obtained from serum of an animal which has been immunized by using the Hfzo protein of the invention (1) as an antigen. As the antigen, peptides that are chemically synthesized based on the amino acid sequence represented by SEQ ID NO: 2 or SEQ ID NO: 4, Hfzo proteins that are expressed in eukaryotic cells or prokaryotic cells can be used. Alternatively, the antibody may be prepared by sampling serum after introducing the aforementioned expression vector for eukaryotic cell into muscle or skin of animal by injection or gene gun (for example, invention disclosed in Japanese Patent Application Publication (JP-A) No. 7-313187). As the animal, mouse, rat, rabbit, goat, chicken and the like can be used. By preparing a hybridoma by fusing a B cell sampled from a spleen of immunized animal with a myeloma, it is possible to produce a monoclonal antibody against the Hfzo protein.

The invention (8) provides a proteoliposome composed of the Hfzo protein of the invention (1) and lipid, and can be used as a liposome vector which encapsulates foreign genes or drugs so as to achieve mitochondrial specific gene transfer or drug administration. In brief, inventors of the present invention created proteoliposome using a membrane fraction of mouse hepatocyte mitochondria and lipid, encapsulated a fluorescent pigment marker in the proteoliposome, and microinjected the proteoliposome into a mouse fertilized egg, and finally found that the localization of inherent mitochondria coincides with the localization of liposome (Biochem, Biophys, Res. Comm. 278: 183-191, 2000). This suggests that mitochondrial membrane protein constituting the liposome recognizes the same membrane protein of inherent mitochondrial and bind thereto, thereby causing aggregation and fusion of liposome and inherent mitochondria.

Such a proteoliposome can be constructed by preparing a liposome in a known manner, and mixing the aforementioned Hfzo protein according to the invention (1) with this liposome, followed by freezing, melting and the like operations.

EXAMPLES

Now the present invention will be explained more concisely and concretely by way of examples, however, it is to be noted that the present invention is not limited to these examples.

EXAMPLE 1

Cloning of cDNA

A human EST library was searched on the basis of the base sequence of cDNA of *drosophila* Fzo gene (Cell 90: 121-129, 1997; GenBank Accession No. U95821), and using highly homologous ESTs as probes, a cDNA library derived from human heart was searched. As a result of this, two positive clones were obtained. 5' side and 3' side were synthesized in accordance with RACE (Rapid amplification of cDNA ends) method, to obtain two complete long cDNA sequences (Hfzo1 and Hfzo2).

Hfzo1 had a total length of 2754 bp (SEQ ID NO: 1), and its ORF encoded Hzo1 protein made up of 741 amino acid residues (SEQ ID NO: 2) and having a molecular mass of about 84 kD. Hfzo2 had a total length of 2754 bp (SEQ ID NO: 3), and its ORF encoded Hzo1 protein made up of 769 amino acid residues (SEQ ID NO: 4) and having a molecular mass of about 87 kD.

Both of these proteins were identified as a GTPase having transmembrane domains. Specifically, as to the Hfzo1, transmembrane domains were found at the positions 595-607 and 614-628 in SEQ ID NO: 2, while as to the Hfzo2, transmembrane domains were found at the positions 623-635 and 642-656 in SEQ ID NO: 4. The GTPase active site of Hfzo1 was found at the position 76-268 in SEQ ID NO: 2, while the GTPase active site of Hfzo2 was observed at the position 104-296 in SEQ ID NO: 4. In addition, Coiled Coil domains were observed at the positions 360-404 and 689-734 in SEQ ID NO: 2 for Hfzo1, and at the positions 388-432 and 717-762 in SEQ ID NO: 4 for Hfzo2. Furthermore, these genes have alternative splicing at their 5' terminal exons, and in particular, Hfzo2 protein has a structure predictable as a mitochondrial target signal (position 1-31 in SEQ ID NO: 4).

EXAMPLE 2

Expression of Hfzo cDNA in HeLa Cell

Polynucleotides comprising base sequences constituting ORF regions of SEQ ID NO: 1 and SEQ ID NO: 3 were individually inserted into expression vectors (pCMV-SPORT) and coupled thereto, and the resultant recombinant vectors were introduced into HeLa cells, the HeLa cells were stained with rhodamine 123, and the condition of mitochondria was observed.

Figure 1:
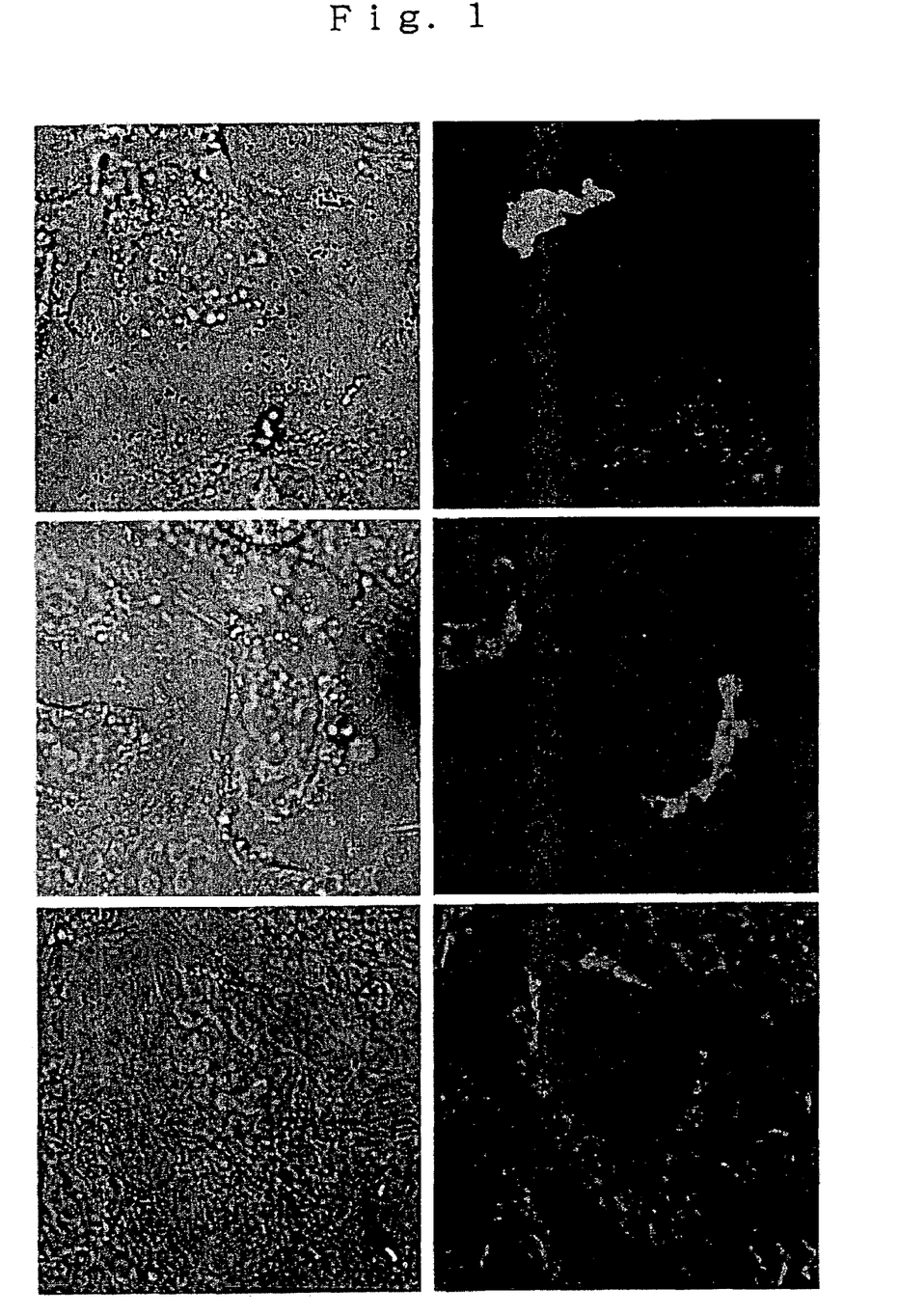
FIG. 1 is a photographic image taken with a confocal laser scanning microscope, showing the condition of mitochondria stained with rhodamine123 in a HeLa cell into which cDNA of Hfzo genes has been introduced.

The result is shown in FIG. 1. In FIG. 1, the upper stage shows a bright-field image and the lower stage shows a dark-field image. From these images, it was demonstrated that mitochondria aggregate in the vicinity of nuclei in the HeLa cell into which either cDNA of Hfzo1 or cDNA of Hfzo2 has been introduced (middle lane and right lane, respectively), in contrast to the control (left lane) where reticulum mitochondria are observed throughout the cytosol. Also, electromicroscope observation of HeLa cell into which Hfzo2 cDNA has been introduced demonstrated partial induction of mitochondrial inner membrane.

From these results, it was confirmed that the Hfzo1 and Hfzo2 proteins of the present invention have the function of promoting aggregation and fusion of mitochondria.

In addition, point mutation analysis with respect to the GTPase active site demonstrated that aggregation of mitochondria depends on GTPase activity.

EXAMPLE 3

Expression of Hfzo cDNA-GFP Fusion Protein in HeLa Cell

GFP was coupled to a carboxylic terminal of polynucleotides comprising either of the base sequences constituting ORF regions represented by SEQ ID NO: 1 and SEQ ID NO: 3, and the resultant polynucleotide was inserted and coupled into an expression vector (pCMV-SPORT: Life Technologies), to create a plasmid. The plasmid was co-expressed in a HeLa cell with pDs Red1-Mito plasmid (Clontech) encoding red fluorescent protein having a mitochondrial target signal. Using a confocal laser scanning microscope, mitochondria were observed by red fluorescence and Hfzo1-GFP and Hfzo2-GFP fusion proteins by green fluorescence.

Figure 2:
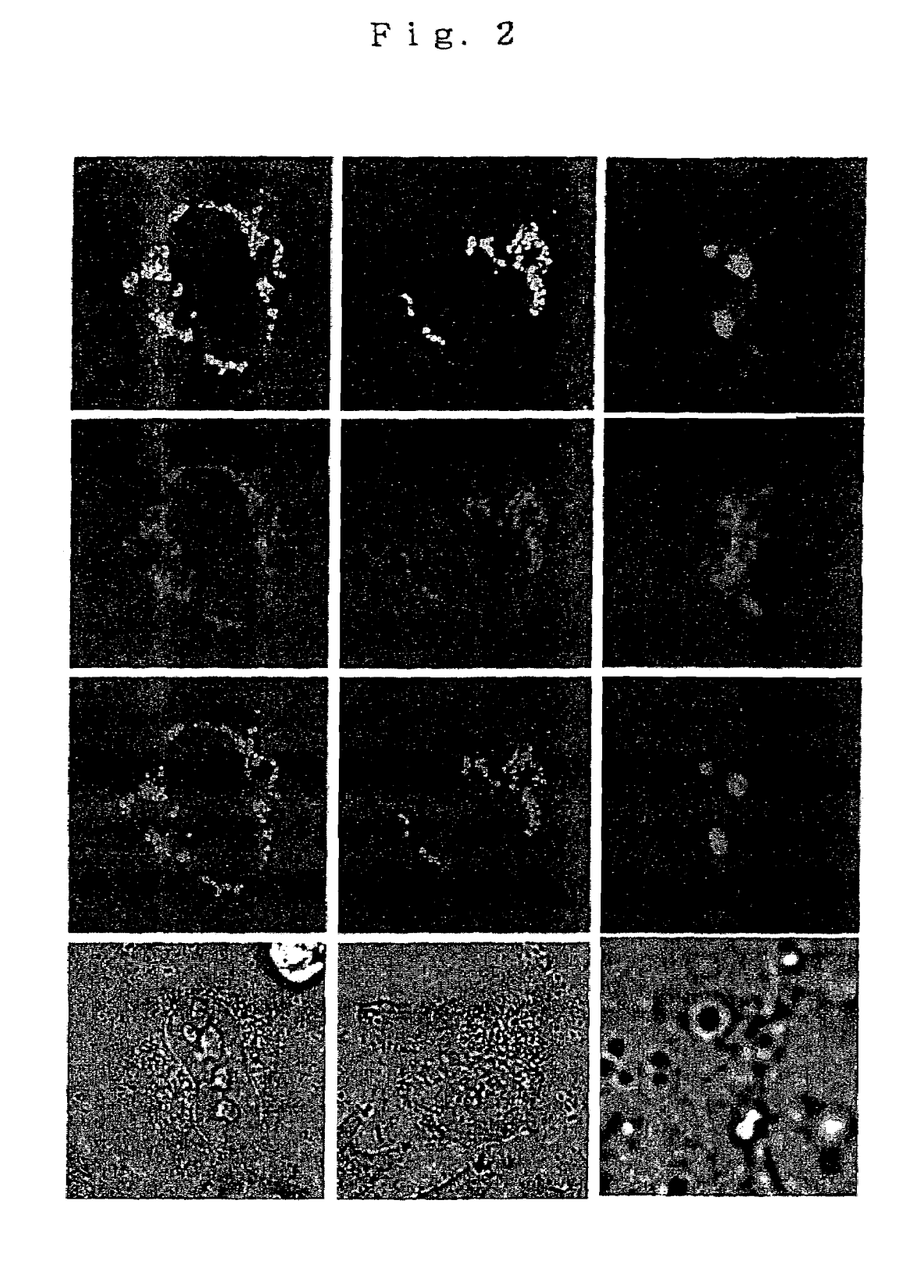
FIG. 2 is a photographic image taken with a confocal laser scanning microscope, showing the mitochondria and localization of Hfzo-GFP fusion proteins in a HeLa cell into which pDs Red1-Mito gene encoding red fluorescent protein having a mitochondrial target signal and Hfzo-GFP fusion genes have been introduced.

The results are as shown in FIG. 2. In FIG. 2, the first (in a left-to-right order) lane shows bright-field image, the second lane shows Hfzo-GFP fusion protein observation image (green fluorescence), the third lane shows mitochondria observation image (red fluorescence) and the fourth lane shows a simultaneous observation image of mitochondria and Hfzo-GFP fusion protein. The upper stage shows the HeLa cell into which Hfzo1-GFP cDNA has been introduced, and the middle stage shows the HeLa cell into which Hfzo2-GFP cDNA has been introduced. The lower stage shows an image of mitochondria portion of the HeLa cell into which Hfzo2-GFP cDNA has been introduced, observed at strong magnification. As is apparent from FIG. 2, it was confirmed that both of the Hfzo proteins locate on mitochondrial membrane, and specifically locate at the site where mitochondria aggregate and contact with each other.

EXAMPLE 4

Preparation of Recombinant Hfzo2 Protein

Host *Escherichia coli* BL21 was transformed with an expression vector (pQE and pGEX) into which a polynucleotide comprising the base sequence constituting the ORF region of SEQ ID NO: 3 had been inserted. The bacterial cells were cultured for 5 hours at 37° C. in LB medium, added with IPTG in a final concentration of 0.4 mM, and cultured for another 2.5 hours at 37° C. Bacterial cells were separated by centrifugation, dissolved in a lysis buffer (50 mM Tris HCl (pH7.5), 1 mM EDTA-1% Triton X-100, 0.2% SDS, 0.2 mM PMSF), frozen at −80° C. and melted, and then crushed by ultrasonication. The crushed substances were centrifuged, and Hfzo2 protein was separated and purified from the supernatant.

EXAMPLE 5

Preparation of Proteoliposome 10 mg of soybean phospholipid was dissolved in 1 mL of chloroform, and 50 µl of the solution was evaporated to give a pellet. This pellet was hydrated with 100 µL of 75 mM KCl and 10 mM phosphate buffer (pH 7.0), and freezing-melting cycle was repeated three times. Thereafter, the solution was fractionated through a 0.2 µm filter to prepare a liposome. Then this liposome and the purified Hfzo2 protein obtained in Example 4 were mixed in equal amounts, followed by freezing and melting, to prepare a proteoliposome of mono-double layer membrane.

INDUSTRIAL APPLICABILITY

According to the present invention, novel human proteins which promote aggregation and fusion of mitochondria, polynucleotides encoding such proteins, antibodies against such proteins, and proteoliposomes containing such proteins are provided. Human proteins are useful for clarifying causes of mitochondrial diseases as well as for developing preventive and therapeutic methods thereof. Furthermore, antibodies and probes derived from genes encoding such proteins are potentially useful material for diagnosis of condition of mitochondria in particular diseases. Furthermore, proteoliposome provides measures for specific transfer of foreign genes or drugs targeted toward mitochondria.

The invention claimed is:

1. A proteoliposome comprising a human mitochondrial protein, which comprises the amino sequence of SEQ ID NO: 2, and lipid.

* * * * *